United States Patent [19]

Sakimoto et al.

[11] Patent Number: 4,678,710

[45] Date of Patent: Jul. 7, 1987

[54] COATED PARTICULATE MATERIALS AND METHOD FOR MANUFACTURE THEREOF

[75] Inventors: Seiichiro Sakimoto; Kazuo Fujita; Yutaka Yamauchi; Hiroshi Matsue, all of Kawasaki, Japan

[73] Assignee: Showa Denko K. K., Tokyo, Japan

[21] Appl. No.: 790,195

[22] Filed: Oct. 22, 1985

[30] Foreign Application Priority Data

Oct. 22, 1984 [JP] Japan ................. 59-220538

[51] Int. Cl.$^4$ .................. B05D 7/00; B32B 5/16; C08K 9/00; C08F 32/00
[52] U.S. Cl. .................. 428/407; 427/212; 427/221; 523/205; 526/308
[58] Field of Search .............. 427/212, 220, 221; 523/205; 526/308; 428/407; 21/127

[56] References Cited

U.S. PATENT DOCUMENTS 3,561,999  2/1971  Iannicelli ..................... 427/220
3,961,106  6/1976  Heytmeijer et al. ............ 427/220 X
4,148,941  4/1979  Pape et al. ................... 427/220 X

FOREIGN PATENT DOCUMENTS 48-06872  3/1973  Japan .

*Primary Examiner*—Michael R. Lusignan
*Attorney, Agent, or Firm*—Oblon, Fisher, Spivak, McClelland & Maier

[57] ABSTRACT

Coated particulate materials comprise water-soluble particulate materials as cores and a coating deposited on the surface of the particulate materials and formed preponderantly of a copolymer of cyclopentadiene type oligomer and an unsaturated fatty acid oil. Said coated particulate materials are manufactured by coating the surface of water-soluble particulate materials with a copolymer composition of a cyclopentadiene type oligomer and an unsaturated fatty acid oil and subsequently curing the resultant coating.

6 Claims, No Drawings

COATED PARTICULATE MATERIALS AND METHOD FOR MANUFACTURE THEREOF

FIELD OF THE INVENTION AND RELATED ART STATEMENT

This invention relates to coated particulate materials, particularly to caoted pellets, granules, tablets and the like, and to a method for the manufacture of the coated pariculate materials.

The coated pariculate material of the present incention comprises a water-soluble particulate material as the core and a coating deposited on the surface of the particulate material and formed preponderantly of a copolymer of either cyclopentadiene oligomer of an addition product-containing cyclopentadiene oligomer consisting of cyclopentadiene and up to 5% by weight, based on cyclopentadiene, of a chain conjugate diene produced by the Diels-Alder type addition polymerization (hereinafter referred to collectively as "cyclopentadiene type oligomer") and an unsaturated fatty acid oil. The coated particulate materials of the present invention are manufactured by coating the surface of water-soluble particulate materials with a copolymer composition of a cyclopentadiene type oligomer and an unsaturated fatty acid oil and subsequently curing the resultant coating. The coated particulate materials so manufactured are characterized by their ability to control the amount of the water-soluble component of the cores dissolving out into water.

Fertilizers, herbicides, medicines, etc. by nature are required to release their principal components at controlled speeds; rapid in some applications and slowly in other applications. This invention fulfills this requirement.

Generally, the film-forming substance used in coated particulate materials of the class under discussion is required to possess certain properties:

(a) That it possess high enough hydrophobicity to permit practically sufficient control of the dissolving speed of the water-soluble substances.

(b) That it form a film which is not brittle and can be possessed of sufficient mechanical strength.

(c) That it exhibit sufficient adhesiveness to the water-soluble cores to be coated and, once deposited as a coating on the cores, that it not peel off easily even when the coated granules are exposed to heavy mechanical impacts and wide thermal fluctuations.

(d) That its particles not conglomerate during manufacture or storage.

(e) That it can be produced easily and inexpensively.

As a prior publications concerning coated granules, there can be mentioned U.S. Pat. No. 3,744,987 issued to the assignee of this invention. This patent covers an invention relating to fertilizer pellets having a coating formed preponderantly of phenol resin.

The fertilizer pellets having a coating made of phenol resin are high in cost.

Coated granules which use coatings made of APP (atactic polypropylene), PE, EVA, PE-EVA blend, other similar polyolefins and thermoplastic resins, and sulfur have also been proposed. For example, in the case of APP, the usual practice is to spray APP dissolved in organic solvent onto the granules. The molecular weight of the APP for the coatings is more than 40000. A large amount of organic solvent is necessary for making the solution of APP and the APP content of the organic solution is generally about 5%. Various film-forming substances for use on substrates have been developed as described above. Unfortunately, they are deficient in varying aspects as described above. The desirability of perfecting coated particulate materials which are produced without large consumption of a solvent and are furnished with a coating not brittle but capable of providing easy control of the release of the principal component without entailing the drawbacks suffered by the conventional coated particulate materials as described above and a method for the manufacture of the coated particulate materials has been in strong demand.

OBJECT AND SUMMARY OF THE INVENTION

An object of this invention is to provide coated particulate materials which permit easy control of the release of the principal component thereof and retain the coating thereof intact throughout the entire course of the release and which are easily produced.

Another object of this invention is to provide a method for the manufacture of the coated particulate materials described above.

To be specific, the coated particulate materials of the present invention comprise (A) water-soluble particulate materials and (B) a coating deposited on the entire surface of the aforementioned particulate materials and consisting essentially of a copolymer of (a) either (1) cyclopentadiene oligomer or (2) an addition product-containing cyclopentadiene oligomer formed of cyclopentadiene and up to 5% by weight, based on cyclopentadiene, of a chain conjugate diene formed by the Diels-Alder type addition polymerization and (b) an unsaturated fatty acid oil.

The method of this invention for the manufacture of the aforementioned coated particulate materials comprises causing water-soluble particulate materials heated to 50° to 200° C. to be coated with a copolymer of (a) either (1) cyclopentadiene oligomer or (2) an addition product-containing cyclopentadiene oligomer formed of cyclopentadiene and up to 5% by weight, based on cyclopentadiene, of a chain conjugate diene formed by the Diels-Alder type addition polymerization and (b) an unsaturated fatty acid oil heated and fused in advance at 40° to 250° C. and subsequently curing to dryness the resultant coating.

DETAILED DESCRIPTION OF PREFERRED EMBODIMENTS

As resins using cyclopentadiene as a raw material, alkyd resins and resins of copolymers of cyclopentadiene with animal and vegetable oils are known in the art. The resins using cyclopentadiene or dicyclopentadiene are a raw material generally produced using higher pressure reactors. The resin to be used in this invention for the formation of the coating is a copolymer of the oligomer of cyclopentadiene and an unsaturated fatty acid oil and the resin is made under atmospheric pressure. When this resin is applied on the surface of water-soluble granules and then subjected to oxidative polymerization, it is converted into a cross-linked reticular superpolymer in the form of a coating. This copolymer, when heated and fused, exhibits a low visicosity in the range of 2000 to 100 cps at 150° C. and, therefore, permits the coating to be formed completely even by direct application to the surface of particulate materials through spraying without use of a solvent such as toluene or xylene. The coating formed after the curing possesses ample mechanical strength, provides practically sufficient control of the release of the principal component, exhibits satisfactory adhesiveness to the substrate, and suffers no conglomeration of component particles during manufacture or storage. Thus, the coated particulate materials can be obtained easily and inexpensively.

Further, since no solvent is required, the manufacture of the coated particulate materials by the method of this invention has a high economic advantage in that the equipment used therefor is simple and does not require a large investment. It is also free from the trouble otherwise involved in recovery of used solvent, the danger of fire and explosion, and the problems otherwise posed where any organic solvent is used. The coating of polymer film obtained after the curing possesses gloss and transparency, so that the produced coated particulate materials are excellent in appearance and have high commercial value.

Now, the present invention will be described more specifically below. The cyclopentadiene type oligomer is formed of either cyclopentadiene or dicyclopentadiene with up to 5% by weight, based on cyclopentadiene, of the Diels-Alder type addition polymerization product of an unsaturated compound. Desirably, the molecular weight of this cyclopentadiene type oligomer is in the range of 200 to 5000. If the molecular weight of the oligomer fails to reach the lower limit 200, the coating formed of the copolymer of the oligomer with the unsaturated fatty acid oil (hereinafter referred to collectively as "copolymer") is brittle and the speed of curing of the coating by drying is intolerably slow.

If the molecular weight of the oligomer exceeds 5000, the copolymer possesses a high melt viscosity and, therefore, suffers from poor workability.

The aforementioned term "unsaturated compound" means a compound possessing a double bond or triple bond capable of the Diels-Alder type addition reaction with cyclopentadiene or dicyclopentadiene. Generally, these compounds are referred to as dienophiles. They embrace compounds which have carbonyl, nitrile, nitro, halogen, acetoxy, phenyl, sulfon, oxymethyl, aminomethyl, cyan methyl adjoining unsaturated bonds and butadiene, pentadiene, isoprene and alkyl butadiene, for example.

Optionally, the copolymerization of the cyclopentadiene type oligomer and the unsaturated fatty acid oil may be made to occur in the presence of a saturated or unsaturated polybasic acid or anhydride or a polyhydric alcohol so that the copolymerization will proceed simultaneously with interesterification or polyesterification.

The term "unsaturated fatty acid oil" refers to a triglycerin ester, diglycerin ester, or monoglycerin ester of a saturated fatty acid such as, for example, palmitic acid or stearic acid containing at least one unsaturated fatty acid of chain structure selected from among the carboxylic acid, RCOOH, possessing at least one carboxylic group and at least one unsaturated double bond. Concrete examples of the fatty acid oil are half-dry oils and dry oils such as soybean oil, linseed oil, cottonseed oil, rapeseed oil, and tung oil.

Concrete examples of the unsaturated fatty acid are acrylic acid, crotonic acid, isocrotonic acid, undecylenic acid, oleic acid, elaidic acid, cetoleic acid, erucic acid, brassidic acid, sorbic acid, linolic acid, linolenic acid, and arachidonic acid.

Concrete examples of the saturated and unsaturated polybasic acids and anhydrides allowed to be present in the copolymerization system are phthalic acid, phthalic anhydride, isophthalic acid, adipic acid, tetrahydrophthalic anhydride, tetrahydro-phthalic acid, endomethylene-tetrahydro-phthalic acid and anhydride, HET acid, maleic acid, maleic anhydride, fumaric acid, and itaconic acid.

Concrete examples of the polyhydric alcohol such as glycol allowed to be present in the copolymerization system are ethylene glycol, propylene glycol, diethylene glycol, trimethylene glycol, glycerin, neo-pentyl glycol, and 1,1-isopropylidene-bis(p-phenyleneoxy)-di-2-propanol.

There are times when the cyclopentadiene type oligomer may be made to react first with acrylic acid, methacrylic acid or an ester thereof, acrylonitrile, or maleic anhydride and subsequently with the unsaturated fatty acid oil. An example of the copolymerization will now be described. One part of cyclopentadiene oligomer, 0.5 to 3 parts, preferably 0.5 to 1.5 parts, of soybean oil, and 0.05 to 0.2 part of maleic anhydride as the raw materials are charged into a reactor and simultaneously, stirred and heated. The reaction temperature is in the range of 220° to 280° C., preferably 240° to 270° C. If the temperature falls short of the lower limit of the aforementioned range, the reaction continues for a prolonged period. If this temperature exceeds the upper limit, or particularly the level of 290° C., there ensues the disadvantage that the cyclopentadiene oligomer undergoes conspicuous thermal decomposition.

The reaction time of copolymerization, though variable with temperature, generally falls in the range of 3 to 7 hours when the heating temperature is on the order of 250° to 270° C. The reaction can be carried out under atmospheric pressure. The volatile component which is produced during the reaction is desired to be thoroughly removed. It is important that, during the reaction, the reactor be kept sealed with nitrogen gas to prevent the resin from oxidation and, at the same time, preclude explosion of the gaseous phase. Although the progress of the copolymerization can be checked with the acid number, bromine number, and melt viscosity of the resin, it can be controlled by continuously measuring the melt viscosity of the resin at a fixed temperature, for example, 150° C. Control based on this principle is simple and practical. In this case, it is naturally necessary that the correlation between the melt viscosity and the physical properties of the finally produced coating be determined in advance.

The molten resin which has undergone the reaction is cooled to a temperature in the range of 100° to 160° C. and then mixed with a dry catalyst. The catalyst used for this purpose is generally a naphthenate of manganese, cobalt, iron, lead, or nickel. The amount of the catalyst to be used is in the range of 0.005 to 0.1 part as naphthenate per part of the resin.

Generally, the naphthenate contains a catalytic metal in a concentration of 1 to 10%. During the mixture of the molten resin with the catalyst, the reactor must be kept sealed with nitrogen gas to prevent the resin from oxidation. The resin produced by the procedure described above is excellent in transparency and chromaticity.

The particulate materials to be coated with the resin of this invention are not specifically defined. The resin is essentially aimed at providing a coating capable of manifesting the effect of permitting gradual release of principal components from particulate materials of fertilizer, herbicide, combination of fertilizer and herbicide, fungicide, and rustproofing agent. Practically, the particulate materials are desired to have solubility of not less than 0.5% in water at 30° C. and particle diameters not less than 0.5 mm and not more than 50 mm.

Concrete examples of the water-soluble particulate materials contemplated by this invention include ammonium sulfate, ammonium chloride, ammonium nitrate, potassium nitrate, calcium nitrate, potassium chloride, potassium sulfate, potassium carbonate, sodium phosphate, potassium phosphate, ammonium phosphate, urea, phenoxy acetic acid, phenoxy propionic acid, phenoxy butyric acid, 4-amino-3,5,6-trichloro-picolinic acid, S-triazine, and phenoxyethyl-sulfuric acid. They may incorporate Mg, Mn, B, etc. as trace elements.

Now, the method of this invention for the manufacture of the coated particulate materials will be described below.

In the present invention, the copolymer of the cyclopentadiene type oligomer and the unsaturated fatty acid oil is used as the film-forming substance. In this case, the ratio of the amount of the cyclopentadiene type oligomer to that of the unsaturated fatty acid oil in the copolymer generally is in the range of 0.2 to 5 parts of the latter to 1 part of the former. If this ratio fails to reach the lower limit the coating film formed of copolymer is frequently brittle. If it exceeds the upper limit, the curing speed of the coating by drying is slow.

Then, the water-soluble particulate materials are heated to a temperature in the range of 50° to 200° C. and the aforementioned copolymer is heated and melted at a temperature in the range of 40° to 250° C. The hot water-soluble particulate materials are then coated with the molten copolymer and then the coated particulate materials are blown with hot air at a temperature in the range of 40° to 200° C. to dry and cure the coating.

The coating of the water-soluble particulate materials with the molten copolymer can be effected by spraying the molten copolymer of the cyclopentadiene type oligomer and the unsaturated fatty acid oil onto the fluidified water-soluble particulate materials or by keeping the particulate materials rolled inside a rotary tumbler or a pan type tumbler and spraying them with the molten copolymer, for example.

Now, the method as actually applied to the manufacture of coated granules of compound fertilizer will be described.

Granules of compound fertilizer containing at least two fertilizing components such as nitrogen, phosphoric acid, and potassium are kept rolled in a rotary drum or a pan type coater and heated by hot blast to a temperature in the range of 50° to 150° C., preferably 120° to 140° C.

Separately, in a vessel part of the copolymer resin prepared from soybean oil and cyclopentadiene oligomer of an average molecular weight of 900 and 0.03 part of manganese naphthenate having a Mn content of 10% are melted and mixed at 150° C. The molten mixture roughly formed in the vessel is taken out and placed in a tank fitted with a spray pump. In this tank, the molten resin is kept adjusted to 150°±5° C. with an electric heater. The pipes for passing the molten resin are also kept warmed with a heater or the like. The pipes are each provided with a spray nozzle tip at their leading end.

The spray pump is electrically or pneumatically driven to force the molten resin through the spray nozzle and deposit it on the granules. The spray nozzle can be suitably selected depending on the spray pattern, the coating thickness, the melt viscosity, and the ease of oxidative polymerization. It is important that the spray should be accomplished by liquid pressure of the molten resin without use of air. Examples of the sprayer usable for this purpose are an airless spray unit and a hot melt applicator. Optionally, the deposition may be accomplished by simply pouring the molten resin on the substrate.

The molten resin is sprayed on the granules of fertilizer at the rate of 1 to 15% based on the amount of the granules, with the granules being rolled constantly during spraying. The resultant coated granules are dried with hot blast at a temperature in the range of 80° to 150° C.

The spraying with the molten resin may be carried out in one round or, preferably in two to five rounds to ensure thorough oxidative curing of the applied coating.

When the spraying is performed in two or more rounds, the coated granules are required to be dried and cured with hot blast for 3 to 30 minutes in each of the intermissions. The amount of the molten resin to be sprayed in each round is suitably fixed, e.g., on the basis of the speed of release of the principal component required of the final product. In any event, it is important that the applied molten resin should thoroughly cover the surface of the finally produced granules of fertilizer and should be amply cured so as to heighten the efficiency of the resin to be used and enable stable release of the water-soluble principal component from the product. The granules of compound fertilizer so produced provide controlled release of the principal component of fertilizer over a long period and retain their desirable gloss intact. The rate of the release of the principal component can be suitably controlled by selecting the kind of the resin of the coating, the thickness of the applied coating, and the degree of crosslinking of the coating.

In the case of other granules than those of fertilizer, the kind of resin, the thickness of coating, the degree of crosslinking, the temperature of spraying, the temperature of curing, etc. should be selected, considering the thermal stability of the substance in the granules and the extent of the desired control of the rate of release.

The coated particulate materials of this invention possess a coating which essentially consists of a copolymer of cyclopentadiene oligomer and an unsaturated fatty acid oil.

Now, the present invention will be described more specifically below with reference to working examples.

EXAMPLE 1

(Preparation of resin)

An autoclave of stainless steel having an inner volume of 500 liters and provided with stirring blades, a thermometer, a cooling coil, a nitrogen gas inlet tube, a gas discharge tube, a trap device, and a heater unit was charged with the following ingredients. Cyclopentadiene oligomer (average molecular weight 900) 140 kg
Soybean oil: 140 kg
Maleic anhydride: 2 kg
Under a feeble flow of nitrogen gas, the ingredients in the autoclave were molten at 80° C.

The reaction temperature was further raised to 270° C. and the stirring was continued under a current of nitrogen for five hours. The reaction was continued at 260° to 270° C. From the water cooling trap connected to the gas discharge tube, 2.2 kg of distillate was collected. This distillate was preponderantly of dicyclopentadiene. The product was mixed with 5 kg of manganese naphthenate having a Mn content of 10% and then allowed to cool to 150° C. for one hour under a current of nitrogen. The copolymer resin produced before the addition of manganese naphthenate had an acid number of 11.22 and a melt viscosity of 100 cps (as measured with a B type rotatory viscosimeter at 150° C.)

50 kg of the Mn-containing copolymer resin in the molten state at 150° C. was discharged through the bottom nozzle of the autoclave into a hot melt applicator, Model 11J, made by NORDOSON Corp. The hot melt applicator was kept warm so as to retain the molten copolymer resin at 150° C.

Separately, in a pan coater, 250 kg of granules of compound fertilizer, N—$P_2O_5$—$K_2O$, 14—14—14, having an average particle diameter of 1.5 to 2 mm were rolled and heated to 110° C. with hot air.

The molten copolymer resin was sprayed onto the hot rolling granules of fertilizer in a pan-coater by the spray gun of a hot melt applicator having a spraying liquid pressure of 2.5 kg/cm². The amounts of the molten resin so sprayed in the three cycles each consisting of 5 minutes' spraying and 15 minutes' drying were 7.5 kg, 5 kg, and 5 kg respectively. By the heat of oxidative polymerization, the temperature of the coated granules of fertilizer reached a level in the range of 120° to 125° C. By cooling the coated granules, there were obtained coated granules of fertilizer. The coated granules were tested for release of the principal component under water at 30° C. The results are shown below.
Amount of release after one month's standing: 28%
Amount of release after two months' standing: 52%
Amount of release after three months' standing: 82%

EXAMPLE 2

A compound fertilizer containing 12% of $NH_3$—N, 12% of $P_2O_5$, and 12% of $K_2O$ was blended, comminuted, and compressed to tablets 8 mm in diameter. The pressure used for the compression was 2 tons/cm².

In the same pan coater as used in Example 1, 250 kg of the tablets were kept rolled and heated to 80° C. Onto the rolling tablets, the molten copolymer resin maintained at 90° C. was sprayed six times, by the same cycle as in Example 1, with the spray gun of an airless spray unit. Consequently, there were obtained coated granules of fertilizer. The amounts of the molten resin so applied by sprying were 1 kg/cycle. The copolymer resin used for coating the granules was prepared by the reaction of the following ingredients in the same autoclave as used in Example 1.
Cyclopentadiene oligomer (average molecular weight 400): 120 kg
Tung oil: 120 kg
Pentaerythritol: 5 kg
Maleic anhydride: 2 kg
Phthalic anhydride: 1 kg The reaction temperature was further raised to 260° C. and maintained at 260° C. for 5 hours under a slow flow of nitrogen. As a dry catalyst, 2 kg of manganese naphthenate and 2 kg of cobalt naphthenate containing 10% of Mn and Co respectively were added and melted.

The coated granules of fertilizer so produced were tested for release of principal component under water by the method of Example 1. The results are shown below.
Amount of release after one month's standing: 57%
Amount of release after two months' standing: 77%
Amount of release after three months' standing: 85%

EXAMPLE 3

With a suitable amount of water, 18 parts of talc, 1 part of corn starch, and 1 part of phenoxy-acetic acid were intimately blended and extruded with a extruder. The extruded ribbon of mixture was cut into pellets and dried in flowing air at room temperature, to afford pellets 2 mm in diameter and 3 mm in length. In the same pan coater as used in Example 1, 100 kg of the pellets were kept rolled and heated. Onto the rolling pellets the molten resin was sprayed 4 times by the spray gun of a hot melt applicator at 70° C. in an amount of 500 g/cycle. The cycles each consisted of 3 minutes' spraying and 7 minutes' drying. The temperature of the hot air used for drying was 60° C. The resin used for coating was produced by the reaction of the following ingredients by the method used in Example 1.
Cyclopentadiene of oligomer (molecular weight 300): 100 kg
Cottonseed oil: 50 kg
Glycerin: 5 kg
Adipic acid: 5 kg The reaction temperature was further raised to 240° C. and maintained at 240° C. for 4 hours with stirring under a slow flow of nitrogen. As a dry catalyst, 2 kg of manganese naphthenate and 2 kg of cobalt naphthenate containing 10% of Mn and Co respectively were placed in an autoclave and mixed.

The coated granules were tested for release of principal component under water. The results are shown below.
Amount of release after one month's standing: 18%
Amount of release after two months' standing: 38%
Amount of release after three months' standing: 62%

What is claimed is:
1. Coated particulate materials, comprising:
    (A) water-soluble particulate materials and
    (B) a coating deposited on the entire surface of said particulate materials and consisting essentially of a copolymer of (a) either (1) cyclopentadiene oligomer or (2) an addition product-containing cyclopentadiene oligomer formed of cyclopentadiene and up to 5% by weight, based on cyclopentadiene, of a chain conjugate diene formed by the Diels-Alder type addition polymerization and (b) an unsaturated fatty acid oil
    wherein the ratio of said cyclopentadiene oligomer or said addition-product to said unsaturated fatty acid oil is 0.2–5.0 parts of said oligomer or said addition-product to one part of said unsaturated fatty acid oil, and
    wherein said cyclopentadiene oligomer or said addition-product has a molecular weight in the range of 200–5,000.
2. Coated particulate materials according to claim 1, wherein said water-soluble particulate materials are formed of at least one substance selected from the group consisting of ammonium sulfate, ammonium chloride, ammonium nitrate, potassium nitrate, calcium nitrate, potassium chloride, potassium sulfate, potassium carbonate, sodium phosphate, potassium phosphate, ammonium phosphate, urea, phenoxy-acetic acid, phenoxy-propionic acid, phenoxy-butyrc acid, 4-amino-3,5,6-tri- chloropicolic acid, S-triazine, and phenoxy-ethyl-sulfuric acid.

3. Coated particulate materials according to claim 1, wherein said unsaturated fatty acid oil comprises at least one higher unsaturated fatty acid and at least one member selected from the group consisting of triglycerin esters, diglycerin esters, and monoglycerin esters of saturated fatty acids.

4. A method for the manufacture of coated particulate materials, which comprises coating water-soluble particulate materials heated to 50° to 200° C. with a copolymer of (a) either (1) cyclopentadiene oligomer or (2) an addition product-containing cyclopentadiene oligomer formed of cyclopentadiene and up to 5% by weight, based on cyclopentadiene, of a chain conjugate diene formed by the Diels-Alder type addition polymerization and (b) an unsaturated fatty acid oil wherein the ratio of said cyclopentadiene oligomer or said addition-product to said unsaturated fatty acid oil is 0.2–5.0 parts of said oligomer or said addition-product to one part of said unsaturated fatty acid oil, heated and fused in advance at 40° C. to 250° C. and subsequently curing to dryness the resultant coating, and wherein the molecular weight of said cyclopentadiene oligomer or said addition-product is in the range of 200 to 5,000.

5. A method according to claim 4, wherein said water-soluble particulate materials are formed of at least one substance selected from the group consisting of ammonium sulfate, ammonium chloride, ammonium nitrate, potassium nitrate, calcium nitrate, potassium chloride, potassium sulfate, potassium carbonate, sodium phosphate, potassium phosphate, ammonium phosphate, urea, phenoxy-acetic acid, phenoxy-propionic acid, phenoxy-butyric acid, 4-amino-3,5,6-trichloropicolic acid, S-triazine, and phenoxy-ethyl-sulfuric acid.

6. A method according to claim 4, wherein said unsaturated fatty acid oil comprises at least one higher unsaturated fatty acid and at least one member selected from the group consisting of triglycerin esters, diglycerin esters, and monoglycerin esters of saturated fatty acids.

* * * * *